(12) United States Patent
McIntyre

(10) Patent No.: US 7,252,669 B1
(45) Date of Patent: Aug. 7, 2007

(54) FIXATOR PIN CAP

(76) Inventor: John McIntyre, 137 Bayside Dr., Point Lookout, NY (US) 11569

( * ) Notice: Subject to any disclaimer, the term of this patent is extended or adjusted under 35 U.S.C. 154(b) by 512 days.

(21) Appl. No.: 10/668,953

(22) Filed: Sep. 23, 2003

(51) Int. Cl.
*A61B 17/00* (2006.01)
*A61F 4/00* (2006.01)

(52) U.S. Cl. .............................. 606/54; 606/57; 606/59

(58) Field of Classification Search .................. 606/54, 606/55, 56, 57, 58, 59, 62, 63, 64
See application file for complete search history.

(56) References Cited

U.S. PATENT DOCUMENTS

| | | | |
|---|---|---|---|
| 184,335 A | 11/1876 | Calmus | |
| 494,510 A | 3/1893 | Murphy | |
| 666,281 A | 1/1901 | Morgan | |
| 1,556,966 A | 10/1925 | Selig | |
| 1,837,169 A | 12/1931 | Mazurie | |
| 2,435,850 A | * 2/1948 | Siebrandt | 606/54 |
| 3,160,175 A | 12/1964 | Laemmle | |
| 3,757,826 A | 9/1973 | Kroll | |
| 4,202,378 A | 5/1980 | Bush et al. | |
| 4,564,007 A | * 1/1986 | Coombs et al. | 606/59 |
| 4,604,996 A | * 8/1986 | Nunamaker et al. | 606/54 |
| 4,825,504 A | 5/1989 | Camilleri | |
| 4,976,712 A | * 12/1990 | VanderSlik | 606/59 |
| 5,280,809 A | 1/1994 | Tive | |
| 5,527,309 A | * 6/1996 | Shelton | 606/55 |
| 5,630,815 A | * 5/1997 | Pohl et al. | 606/59 |
| 5,687,772 A | 11/1997 | Underwood | |
| 6,162,224 A | * 12/2000 | Huebner | 606/59 |

* cited by examiner

*Primary Examiner*—Pedro Philogene
(74) *Attorney, Agent, or Firm*—Michael I Kroll

(57) ABSTRACT

The present invention 10 discloses a bridge cap comprising a compressible resilient material having a substantially oval shape with a planar surface on the distal ends 24 thereof. The bridge cap 10 has a cavity 28 with a pliable material 30 therein whereby the bridge cap can be releasably positioned on protruding pins 16 such that the pins extending from the fixator devices can be covered to prevent inadvertent potentially damaging contact with the protruding pins especially while sleeping.

5 Claims, 8 Drawing Sheets

FIXATOR PIN CAP

BACKGROUND OF THE INVENTION

1. Field of the Invention

The present invention relates generally to end protectors and, more specifically, to a bridge cap comprising a compressible resilient material having a substantially oval shape with a planar surface on the distal ends and wherein said bridge gap has a cavity with a pliable material therein whereby said bridge cap can be releasably positioned on protruding pins, such as the pins extending from fixator devices, to prevent inadvertent potentially damaging contact with said protruding pins especially while sleeping.

2. Description of the Prior Art

There are other capping device designed for exposed ends. Typical of these is U.S. Pat. No. 184,335 issued to Calmus on Nov. 14, 1876.

Another patent was issued to Murphy on Mar. 28, 1893 as U.S. Pat. No. 494,510. Yet another U.S. Pat. No. 666,281 was issued to Morgan on Jan. 22, 1901 and still yet another was issued on Oct. 13, 1925 to Selig as U.S. Pat. No. 1,556,966.

Another patent was issued to Mazurie on Dec. 15, 1931 as U.S. Pat. No. 1,837,169. Yet another U.S. Pat. No. 3,160,175 was issued to Laemmle on Dec. 8, 1964. Another was issued to Kroll on Sep. 11, 1973 as U.S. Pat. No. 3,757,826 and still yet another was issued on May 13, 1980 to Bush et al. as U.S. Pat. No. 4,202,378.

Another patent was issued to Camilleri on May 2, 1989 as U.S. Pat. No. 4,825,504. Yet another U.S. Pat. No. 5,280,809 was issued to Tive on Jan. 25, 1994. Another was issued to Underwood on Nov. 18, 1997 as U.S. Pat. No. 5,687,772.

U.S. Pat. No. 184,335

Inventor: Daniel Calmus

Issued: Nov. 14, 1876

A block for the protection of the ends of pipes during transportation that is provided with a shell for protecting the thread on the pipe, substantially as shown.

U.S. Pat. No. 494,510

Inventor: James A. Murphy

Issued: Mar. 28, 1893

An attachment for pencils and like objects, consisting; of a longitudinally slotted tube of flexible, springy material, combined with a cylindrical casing of rubber inclosing said tube, and having an erasing head at one end thereof, combined and operating substantially as set forth.

U.S. Pat. No. 666,281

Inventor: John Henry Morgan

Issued: Jan. 22, 1901

The combination with a tool having a tang, of a handle having; an axial opening to receive said tang, said tang filling said opening tightly at its-end and loosely throughout the main part of the tang, a washer adapted to fit against the end of the handle and close the opening therein, said washer having an opening in line with the opening in the handle but of less diameter, and a ferrule to retain said washer in place, the edges of the opening in said washer being adapted to be forced down and to grip the tang on the insertion of the latter, substantially as described.

U.S. Pat. No. 1,556,966

Inventor: Frank Selig

Issued: Oct. 13, 1925

In a device of the character described, a handle, and a protective tip having axially spaced, resilient handle receiving and centralizing elements conjointly with said handle and tip forming an annular air cushioning chamber.

U.S. Pat. No. 1,837,169

Inventor: Harry R. Mazurie

Issued: Dec. 15, 1931

A protective device for sectional pipe and the like comprising segmental end protectors which are formed with an inner recessed portion to receive a pips end and an outer beveled surface adapted to divert the force of direct blows.

U.S. Pat. No. 3,160,175

Inventor: Richard F. Laemmle

Issued: Dec. 8, 1964

A spacer for use on a conduit comprising a body wing a conduit-receiving socket which is of a cross section complemental to and of a size to receive the conduit, ID socket having a peripheral wall which will surround e conduit and the inner surface of which will engage e outer peripheral surface of the conduit, said peripheral wall having a longitudinally extending rib at one side thereof comprising a heavy portion joined to the wall by thinner web, and a longitudinally extending rib-receiving, spacer and socket portion on the peripheral wall at the opposite side of said body, said rib-receiving spacer and socket portion having a large socket extending longitudinally thereof open at its end and being complemental said rib heavy portion so that its end can be slipped to the end of the large socket, said socket being spaced laterally outwardly of the surface of the peripheral wall the body by a spacer section, said rib-receiving spacer and socket portion having an outer slot opposite the spacer section communicating with said socket and extending longitudinally thereof and having an open end for receiving the end of said web.

U.S. Pat. No. 3,757,826

Inventor: Glenn H. Kroll

Issued: Sep. 11, 1973

An end cap closure assembly for closing the end of a tubular member, particularly the cross bar hanger member of a gym set. The assembly includes a generally hollow body portion having a skirt portion extending therefrom and defining an interiorly facing annular shoulder with the body portion. The skirt portion is adapted to surround the exterior surface of the end portion of a tubular member, for example, the cross bar hanger, with the end thereof abutting the shoulder. The body portion is formed with an opening in the end thereof opposite the skirt portion with the opening communicating with the interior of the skirt portion. An elongated strap member is insertable into the opening formed in the body portion and extends axially beyond the skirt portion. The strap member includes a head portion adapted to close the opening in the body portion and has an aperture formed in the portion of the strap member extending beyond the skirt portion which is adapted to receive fastening means inserted therethrough to secure the assembly to the tubular member.

U.S. Pat. No. 4,202,378

Inventor: Lyman F. Bush et al.

Issued: May 13, 1980

A safety cap for rebar (concrete reinforcing steel) projecting from unfinished construction work protects workmen and passersby from injury resulting from striking the projections. The cap comprises an integral, hollow cylindrical body of resiliently deformable plastic material closed at one end and open at the other. At its closed end the body mounts a radial impact head of enlarged diameter. The open end of the body is split longitudinally to provide an expandable gripping lip. The hollow bore is stepped to provide shoulders accommodating rebar ends of varying diameter.

U.S. Pat. No. 4,825,504

Inventor: Charles F. Camilleri

Issued: May 2, 1989

An end cap for selective installation on rod ends of different diameters. The end cap is a cup-like member having an annular side wall extending between a closed end and an open end. Adjacent the open end, the annular side wall has a substantially cylindrical section which leads to a tapered section of gradually reducing diameter toward the closed end.

U.S. Pat. No. 5,280,809

Inventor: Bruce E. Tive

Issued: Jan. 25, 1994

A breather cap for protecting the ends of tubing and barbed connectors during sterilization and until use in which interference is at a detent spaced from the conduit end, or a positive stop is provided for the conduit end, or a flat handle is provided to facilitate removal of cap from conduit, or two or all of these features are present.

U.S. Pat. No. 5,687,772

Inventor: Daniel C. Underwood

Issued: Nov. 18, 1997

An end cap comprising a hollow base section 11 which can be fitted over the end of a bar. A larger cap section 12 is attachable to the base section 11 to project radially outward therefrom. The base section 11 includes a braced intermediate cap section 13 having a slot 14 into which a bar 14a (shown in phantom) can be fitted using a hand insertable snap action. The intermediate cap section 13 includes an eyelet 15 into which a tab 16 of the cap 12 is fitted as the tab 16 is manually pulled downward as shown in phantom at 17. The enlarged cap section 12 is snap fitted in place via the downwardly projecting legs 18 being forced into the slot 14 so that the shoulders 19 engage the slot.

While these protectors may be suitable for the purposes for which they were designed, they would not be as suitable for the purposes of the present invention, as hereinafter described.

SUMMARY OF THE PRESENT INVENTION

The present invention discloses a bridge cap comprising a compressible resilient material having a substantially oval shape with a planar surface on the distal ends thereof. The bridge cap has a cavity with a pliable material therein whereby the bridge cap can be releasably positioned on protruding pins such that the pins extending from the fixator devices can be covered to prevent inadvertent potentially damaging contact with the protruding pins especially while sleeping.

A primary object of the present invention is to provide a bridge cap for pins protruding from devices.

Another object of the present invention is to provide a bridge cap for the protruding pins of fixator devices.

Yet another object of the present invention is to provide a bridge cap that will protect the wearer from contact with the protruding pins of a fixator device.

Still yet another object of the present invention is to provide a bridge cap for protruding pins from a fixator device whereby the wearer will be protected from injury from said pins while they sleep.

Another object of the present invention is to provide a bridge cap manufactured from a compressible resilient material.

Yet another object of the present invention is to provide a bridge cap having a substantially oval shape.

Still yet another object of the present invention is to provide a bridge cap having a substantially oval shape with the distal ends terminating in planar surfaces.

Another object of the present invention is to provide a bridge cap that will prevent the pins from snagging on clothing.

Yet another object of the present invention is to provide a bridge cap having a cavity with a pliable material therein.

Still yet another object of the present invention is to provide a bridge cap wherein said pliable material forms means for encompassing the distal ends of said protruding pins.

Another object of the present invention is to provide a bridge cap having a substantially oval shape with a pliable core that can be releasably placed on the end of at least one protruding pin.

Yet another object of the present invention is to provide a plurality of bridge caps of varying sizes whereby the user can selectively apply the appropriately sized bridge cap to one or more protruding pins.

Additional objects of the present invention will appear as the description proceeds.

The present invention overcomes the shortcomings of the prior art by providing a bridge cap comprising a compressible resilient material having a substantially oval shape with a planar surface on the distal ends and wherein said bridge cap has a cavity with a pliable material therein whereby said bridge cap can be releasably positioned on protruding pins, such as the pins extending from fixator devices, to prevent inadvertent potentially damaging contact with said protruding pins especially while sleeping.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

Figure 1:
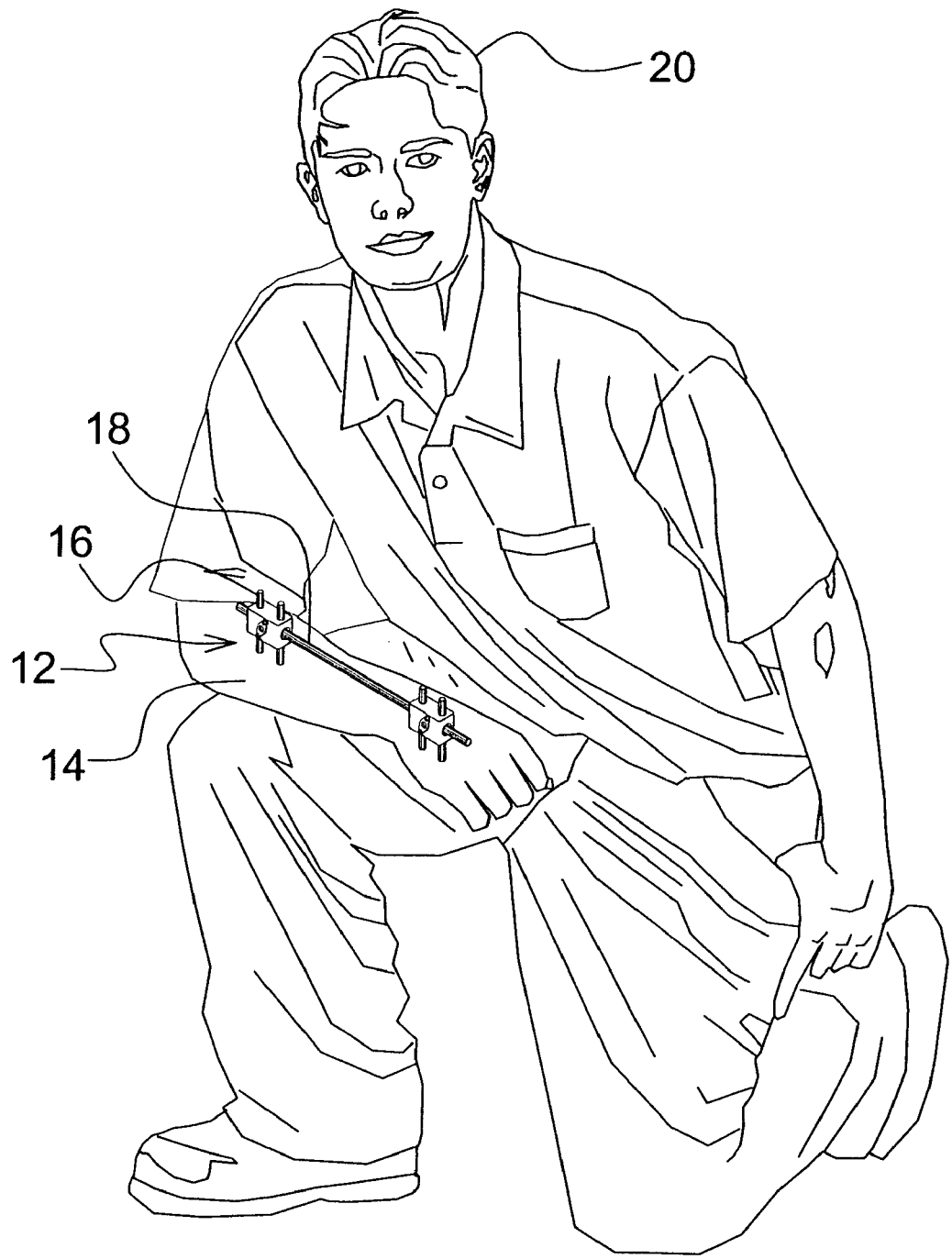
FIG. 1 is an illustrative view of prior art.

With regard to reference numerals used, the following numbering is used throughout 10 present invention
12 external fixator
14 limb
16 fixator pin
18 connecting bar
20 patient
22 blunt surface
24 conical end
26 connecting clamp
28 void
30 pliable material
32 bubble pack

DETAILED DESCRIPTION OF THE PREFERRED EMBODIMENT

The following discussion describes in detail one embodiment of the invention. This discussion should not be construed, however, as limiting the invention to those particular embodiments since practitioners skilled in the art will recognize numerous other embodiments as well. For a definition of the complete scope of the invention, the reader is directed to the appended claims.

Turning to FIG. 1, shown therein is an illustrative view of the prior art. External fixator devices 12 are used to immobilize a limb 14 while healing severe skeletal fractures. The fixator 12 is comprised of a plurality of elements that can be used in various combinations to form an exoskeletal brace or splint. Exposed ends of fixation pins 16 and connecting bars 18 can cause injury to the patient 20. The prior art provides no means of protecting the patient 20 from injury of fixator devices 12.

Figure 2:
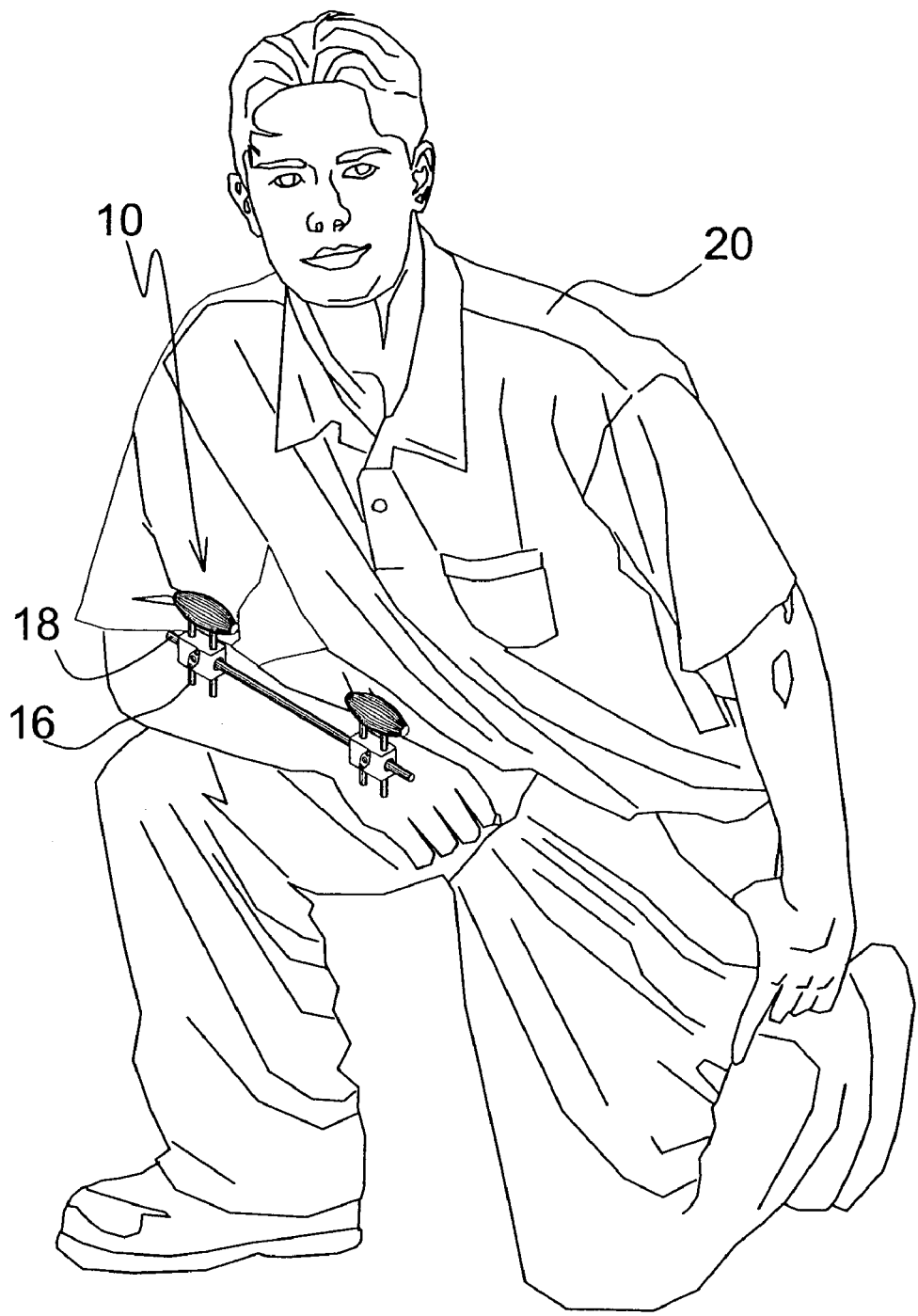
FIG. 2 is an illustrative view of the present invention in use.

Turning to FIG. 2, shown therein is an illustrative view of the present invention 10 in use. The present invention 10 provides an end cap for protection of the patient 20 from the exposed ends of the fixation pins 16 and connecting bars 18. Protruding ends of the pins 16 and shafts 18 can be capped with a soft cylindrical body preventing any injury to the patient. Additionally, the distal ends of the protective member are conically shaped to prevent snagging on clothing.

Figure 3:
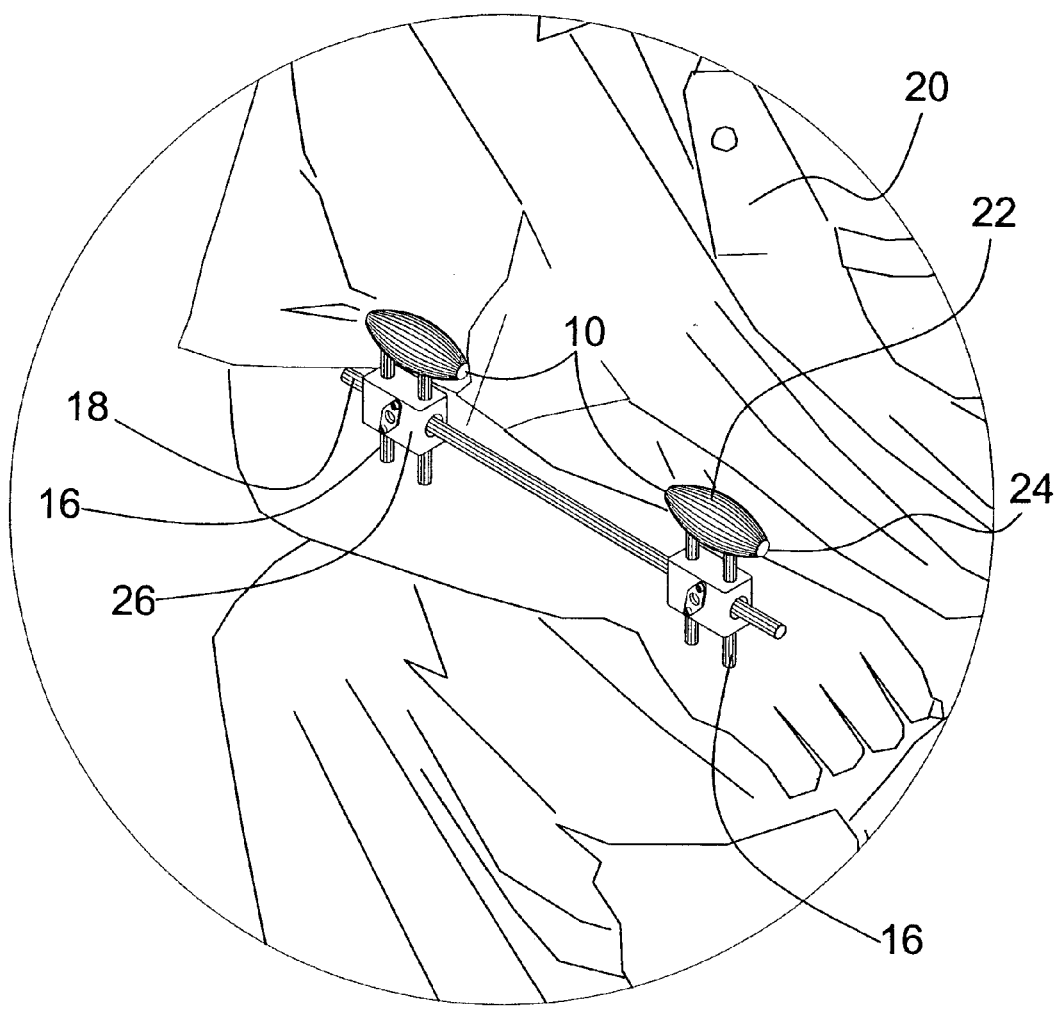
FIG. 3 is an illustrative view of the present invention in use.

Turning to FIG. 3, shown therein is an illustrative view of the present invention 10 in use. Shown is a typical application of the present invention 10 wherein the protective device 10 is place on the exposed ends of the fixation pins 16. A blunt cylindrical surface 22 prevents the user 20 from injury and conical ends 24 prevent snagging on clothing such as shirts or coats. The protective device or bridge cap 10 not only prevents the user 20 from coming into contact with the pins 16 but also creates a space around the pins 16 from contact with other object which could prove painful to the user. Also shown are the connecting bar 18 and connecting clamp 26.

Figure 4:
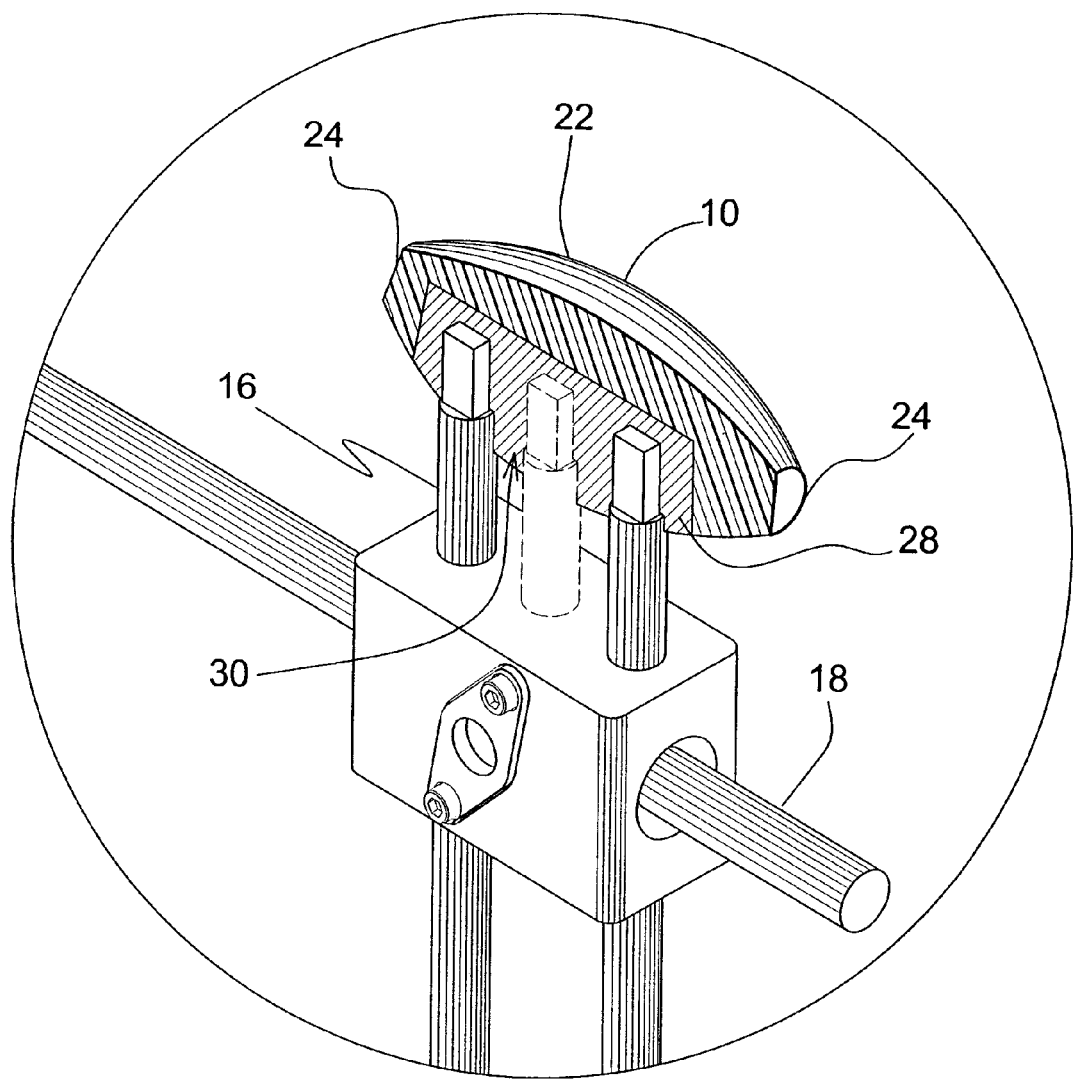
FIG. 4 is an isometric sectional view of the present invention.

Turning to FIG. 4, shown therein is an isometric sectional view of the present invention 10. The present invention 10 or bridge cap is a protective device that is inserted onto the exposed ends of fixator pins 16 to prevent inadvertent contact with the pins especially when sleeping. The protective device 10 is comprised of a cylindrical body 22 with conical ends 24. A rectangular void 28 in the cylindrical body 22 contains a pliable material 30 that will accept and adhere to multiple fixation pin ends 16 at varying pitch distances. Connecting pin 18 is also shown.

Figure 5:
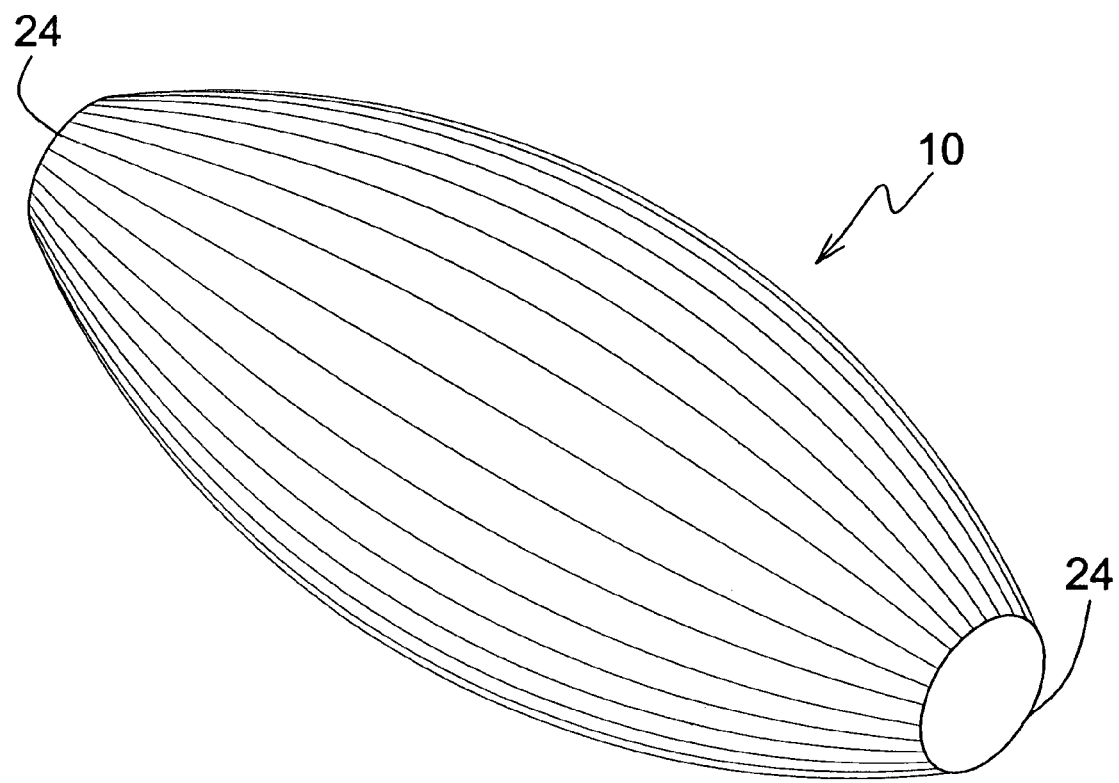
FIG. 5 is an illustrative isometric view of the present invention.

Turning to FIG. 5, shown therein is an illustrative isometric view of the present invention 10. The present invention 10 is a compressible material substantially cylindrical in shape having conical distal ends 24 that can be pressed onto the pins of a fixation device thereby providing protection from the exposed ends of the fixation pins and connecting bars. The protruding ends of the pins and shafts can be capped with a soft cylindrical body preventing any injury especially during sleep. Additionally, the conical distal ends 24 of the protective member prevent snagging on clothing.

Figure 6:
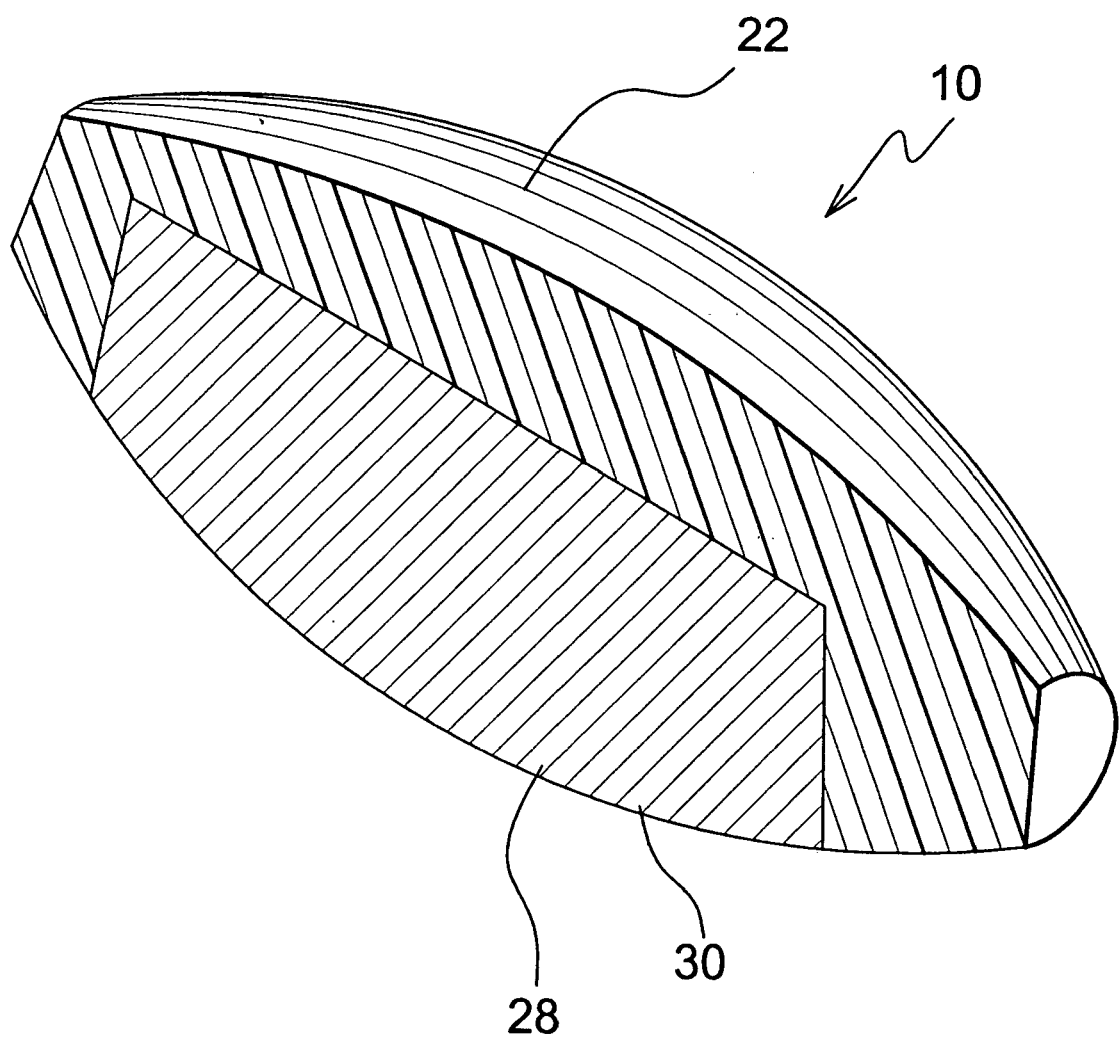
FIG. 6 is an isometric sectional view of the present invention.

Turning to FIG. 6, shown therein is an isometric sectional view of the present invention 10. Shown is a cutaway view of the present invention 10 comprising a compressible housing 22 having a pliable core 30 that can be pressed onto the distal ends of the pins regardless of spacing and angular inclination. To use, the protective device 10 is inserted onto the exposed ends of the fixator pins to prevent inadvertent contact with the pins especially when sleeping. As shown, a rectangular void 28 in the cylindrical housing contains a pliable material 30 that will accept and adhere to multiple fixation pin ends at varying pitch distances.

Figure 7:
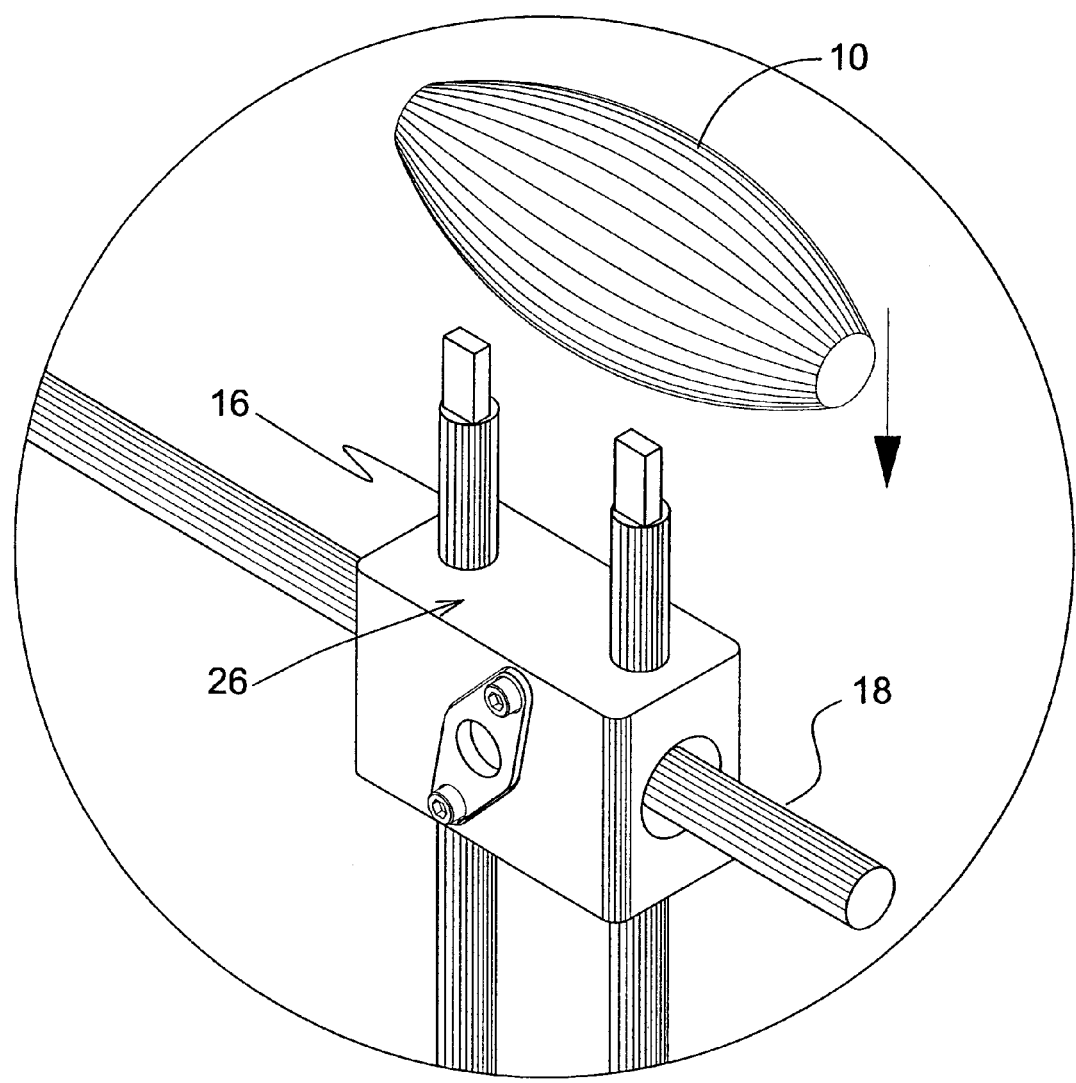
FIG. 7 is an illustrative isometric view of the present invention.

Turning to FIG. 7, shown therein is an illustrative isometric view of the present invention 10. Shown is the present invention 10 or bridge cap providing means whereby a protective element is inserted over the fixation pins 16 of a fixator thereby protecting the user from inadvertently coming into contact with the pins, such as when sleeping. The protective element 10 of the preferred embodiment is frictionally held onto the fixation pins 16. In addition, the protective element 10 is conically shaped on its distal ends to prevent snagging on clothes. Also shown are connecting bar 18 and connecting clamp 26.

Figure 8:
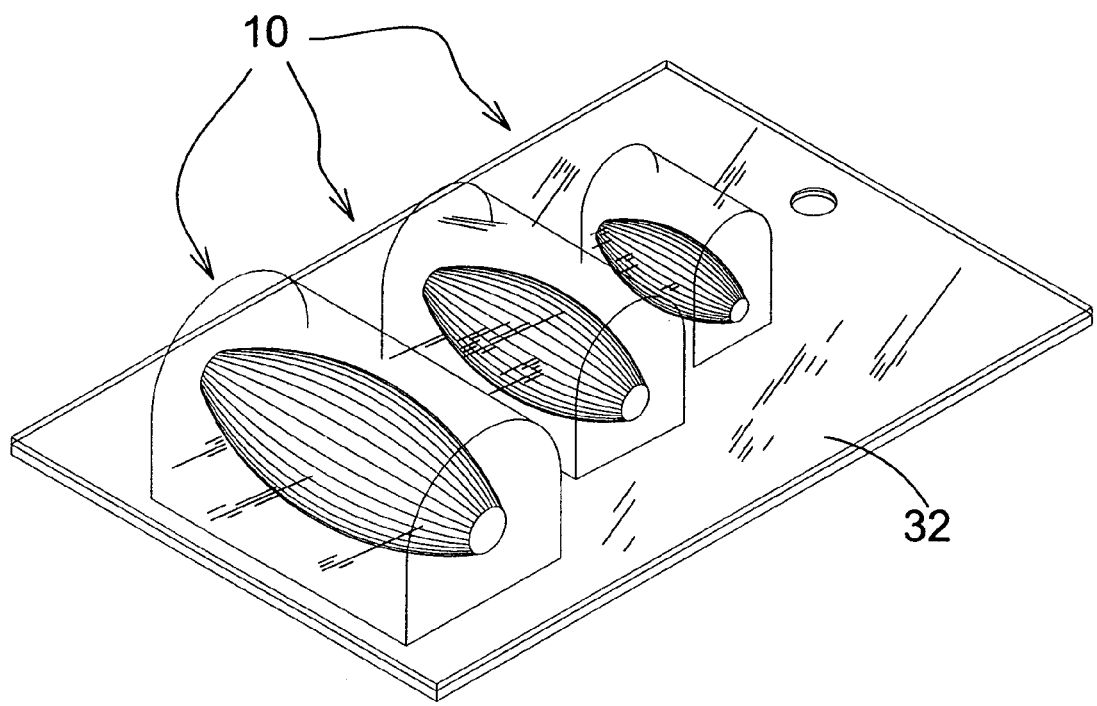
FIG. 8 is an illustrative view of the present invention packaged.

Turning to FIG. 8, shown therein is an illustrative view of the present invention 10 packaged in a bubble pack 32. The present invention 10 can be used for various fixator pins having variable spacing. Shown in the illustration is one means of providing a user with a plurality of different sizes of protective devices 10.

I claim:

1. An end cap for the exposed ends of the pins and rods of an external fixator device, in combination comprising:
   a) a fixator device forming an exoskeletal brace for use on a limb of a patient, said fixator device having at least one connecting rod, a plurality of spaced connecting clamps on said connecting rod, and a plurality of fixation pins extending through each of said connecting clamps, said fixation pins having free ends away from said connecting clamps, said connecting rod having first and second opposing ends;
   b) a separate end cap releasably positioned on said free ends of fixation pins for each connecting clamp leaving a space between end caps;
   c) wherein each said end cap is oval shaped and made of a compressible material and having first and second opposing conically shaped ends and a first and second opposing side surface, said first side surface being generally disposed away from said fixation pins and said second side surface being generally disposed toward said fixation pins, said second side surface having a cavity therein and each of said first and second opposing ends terminating in a planar surface at right angles to a central axis of said end cap; and,
   d) pliable material filling said cavity, wherein said ends of said fixation pins are press fitted into said pliable material to permit the free ends of the fixation pins to be covered, whereby each said end cap before mounting on said free ends of said fixation pins is a solid compressible member containing a filling of pliable material ready for press fitting onto said fixation pins.

2. The end cap of claim 1, wherein said cavity is rectangular shaped and extends from a first point adjacent said first end of said end cap to a second point adjacent said second end of said end cap.

3. The end cap of claim 2, wherein said end cap comprises soft material.

4. The end cap of claim 3, wherein said end cap is manufactured in a plurality of sizes to permit use with various sizes of the fixation device.

5. The end cap of claim 4, further comprising a bubble pack containing said end caps of various sizes ready for direct use.

* * * * *